United States Patent [19]

Brent

[11] 4,281,662

[45] Aug. 4, 1981

[54] OCULAR TESTING DEVICE

[76] Inventor: Allan Brent, c/o Dynamic Systems Design, 145 Palisade St., Dobbs Ferry, N.Y. 10522

[21] Appl. No.: 72,624

[22] Filed: Sep. 5, 1979

[51] Int. Cl.³ .............................................. A61B 5/02
[52] U.S. Cl. .................................. 128/676; 364/417; 128/646
[58] Field of Search ........ 128/687, 672, 676, 645–652, 128/745; 364/415, 417

[56] References Cited

U.S. PATENT DOCUMENTS

| 3,467,837 | 9/1969 | Vick | 128/680 |
|---|---|---|---|
| 3,934,462 | 1/1976 | Rende | 128/652 |

OTHER PUBLICATIONS

Bron, A. J. et al., "Tonographic Studies in Carotid Occlusive Disease", Brit. Jrnl. Opthalmology, (1976), vol. 51, pp. 577–595.

Northrop, R. B. et al., "A No–Touch Ocular Pulse Measurement System for the Diagnosis of Carotid Occlusions," IEEE Trans. Biomed. Engrg., vol. BME–24, No. 2, Mar. 1977, pp. 139–148.

*Primary Examiner*—Robert W. Michell
*Assistant Examiner*—Francis J. Jaworski
*Attorney, Agent, or Firm*—Karl F. Ross

[57] ABSTRACT

A method for diagnosing unilateral internal carotid occlusive disease comprises the application of a vacuum to a patient's left and right eyes and the automatic storage of the negative-pressure magnitudes at which diastolic and systolic pressures of the left and right retinal arteries are attained. Diastolic and systolic percentage differences automatically calculated between the negative-pressure magnitudes stored for the left and right eyes are compared to pre-established standards, whereby unilateral internal carotid occlusive disease may be diagnosed. Calculations are alternatively made using approximate actual retinal-artery pressures automatically calculated according to a predetermined algorithm making corrections for hardening of the arteries owing to increasing age and for differential eye sizes, the age of the patient together with the axial lengths and initial pressures of his eyes being previously stored. Bilateral internal carotid occlusive disease is diagnosable by comparing the calculated actual diastolic and systolic retinal-artery pressures with conventionally measured brachial pressures. A device for controllably applying negative pressure to a patient's eye and automatically calculating pressure differences includes a transducer receiving pressure input from a vacuum generator and transmitting electronic signals to a microprocessor which operates the vacuum generator. The microprocessor is connected to a keyboard for receiving data input, operation-mode instructions and pressure-control signals and to an alpha-numeric display and a bar graph for displaying pressure magnitudes and calculation results.

8 Claims, 7 Drawing Figures

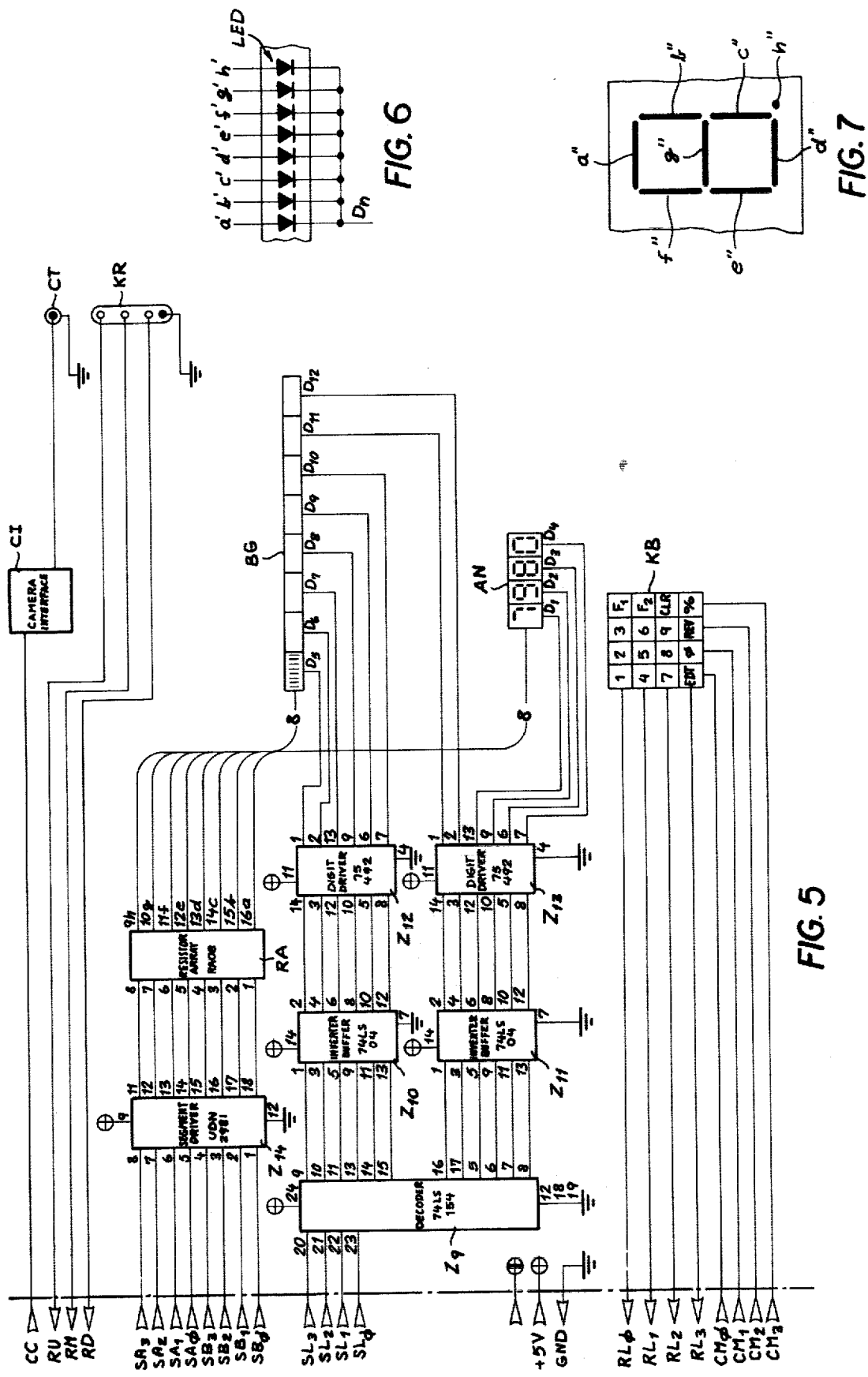

OCULAR TESTING DEVICE

FIELD OF THE INVENTION

My present invention relates to a device for diagnosing internal carotid occlusive disease. In particular, my present invention relates to a device for applying suction to a patient's eyes, whereby internal carotid occlusive disease may be diagnosed.

BACKGROUND OF THE INVENTION

It is a well known fact that a flexible membrane, e.g. a balloon, filled with pressurized air will tend, as nearly as possible given the structural constraints of the balloon, to assume a spherical shape. If a portion of the balloon's surface is forcibly displaced from the position of minimum energy, the pressure inside the balloon will increase. Under this principle, the pressure inside a person's eye may be controllably increased to a point where the diastolic pressure of the retinal artery is no longer great enough to sustain the artery's shape against the aqueous pressure in the eye. Under these circumstances, a pulsation occurs during the systolic pressure increase. If the pressure in the eye is further increased, the retinal artery collapses completely, even the systolic pressure in the artery being insufficient to counteract the pressure induced in the eye by the application of negative pressure to the sclera of the eye.

A device for diagnosing unilateral internal carotid occulsive disease includes a vacuum-generating system for applying negative pressure to the limbal area of a patient's eye via a suction eye cup. The pressure applied to the eye is read by means of a gauge. Thus, an examining physician must operate the vacuum generator and observe the patient's eye for the partial and complete collapse of the retinal artery. In the meantime he must monitor the gauge, or else have an assistant do it for him, and must note the pressure magnitudes at which the diastolic and systolic pressures are attained. Upon performing the test for both eyes, a series of tedious mathematical calculations must be carried out for determining diastolic and systolic negative-pressure differences between the left eye and the right eye. If the differences are of sufficient magnitude, i.e. greater than a predetermined magnitude, an occlusion is diagnosed in the internal carotid artery subsystem for which the negative pressures applied to the respective eye are greater than the pressures applied to the other eye. A more advanced form of this instrument is known in which the gauge is replaced by a digital display; the time required to collect data, however, is not substantially reduced and the calculations are not reduced.

OBJECTS OF THE INVENTION

An object of my present invention is to provide a method of automatically calculating such pressure differences for the diagnosis of internal carotid occulsive disease.

A more particular object of my present invention is to provide such a method for the diagnosis of unilateral internal carotid occulsive disease.

Another particular object of my present invention is to provide such a method for the diagnosis of bilateral internal carotid occlusive disease.

Another object of my present invention is to provide a device for effectively and reliably carrying out these methods.

SUMMARY OF THE INVENTION

According to my present invention, a method of testing a patient for internal carotid occlusive disease comprises the step of applying negative pressure to a surface of one eye of the patient to increase the pressure within the eye to the diastolic and systolic pressures of the retinal artery of the eye. A first magnitude and a second magnitude related to the retinal artery's diastolic pressure and systolic pressure, respectively, are directly and automatically stored. Upon the application of negative pressure to the other eye of the patient to increase intraocular pressure to diastolic and systolic pressure levels, a third magnitude and a fourth magnitude at least partially determined by the diastolic and systolic pressures of the retinal artery of this second-examined eye are directly and automatically stored. Then, a percentage difference between the first and third magnitudes and another percentage difference between the second and fourth magnitudes are automatically calculated, these differences being compared to pre-established limits, whereby an embolism of an internal carotid artery system may be diagnosed.

According to another feature of my present invention, the first magnitude and the third magnitude are the magnitudes of negative pressures being applied to the patient's respective eyes upon attainment of the diastolic pressure of the retinal artery of the respective eye. The second and fourth magnitudes are the values of negative pressures being applied to the eyes upon attainment of the systolic pressure of the retinal artery of the respective eye.

According to another feature of my present invention, a method of testing for internal carotid occulsive disease further comprises the steps of determining the age of the patient and the axial lengths and initial pressures of the respective eyes. The four stored magnitudes related to the diastolic and systolic pressure levels of the patient's eyes are constituted by approximate retinal-artery pressures automatically calculated according to an algorithm making corrections for the hardening of the arteries due to increasing age and for a negative-pressure differential due to variable eye size. Upon the completion of further steps including the measurement of left and right brachial pressures, diastolic and systolic, and the comparison of the calculated retinal-artery pressures to the measured brachial pressures, embolism of both internal carotid artery systems, i.e. bilateral internal carotid occlusive disease, may be diagnosed.

According to yet another feature of my present invention, the magnitudes related to the diastolic and systolic pressures of the left and right retinal arteries may be automatically displayed.

Pursuant to another feature of my present invention, a device for testing a patient for internal carotid occlusive disease comprises a cup engageable with the sclera of a person's eye and a vacuum-generator connected to the cup for applying a negative pressure to an eye surface, whereby intraocular pressure may be raised. A transducer connected to the vacuum generator transmits electronic signals to a microprocessor in response to negative pressures being applied to an eye. The microprocessor directly stores magnitudes at least partially determined by the diastolic and systolic pressures of the retinal arteries of a patient's left eye and right eye and automatically calculates a percentage difference between magnitudes related to the diastolic pressures and another percentage difference related to the systolic pressures. A display shows, under the control of the microprocessor, pressure magnitudes and calculated percentage differences.

Pursuant to another feature of my present invention, the transducer produces analog signals transmitted to a strip chart recorder for the continuous recording of pressure variations and to an analog-digital converter in turn connected to the microprocessor. The analog-digital converter includes a voltage-to-frequency converter feeding square-wave pulses to a counter under the control of the microprocessor.

According to another feature of my present invention, the vacuum generator includes a peristalsis pump and solenoid valves operated by the microprocessor. A keyboard is connected to the microprocessor for feeding the same patient-age and eye-size data and for selecting between a plurality of operation modes.

BRIEF DESCRIPTION OF THE DRAWINGS

These and other features of my present invention will now be described in detail, reference being made of the accompanying drawing in which:

FIG. 5 is a circuit diagram in part illustrating connections between segment and digit drivers and a bar graph and an alpha-numeric display;

FIG. 6 is a circuit diagram of the bar graph shown in FIGS. 1 and 5; and

FIG. 7 is a schematic diagram showing the arrangement of LED segments in the alpha-numeric display shown in FIGS. 1 and 5.

SPECIFIC DESCRIPTION

Figure 1:
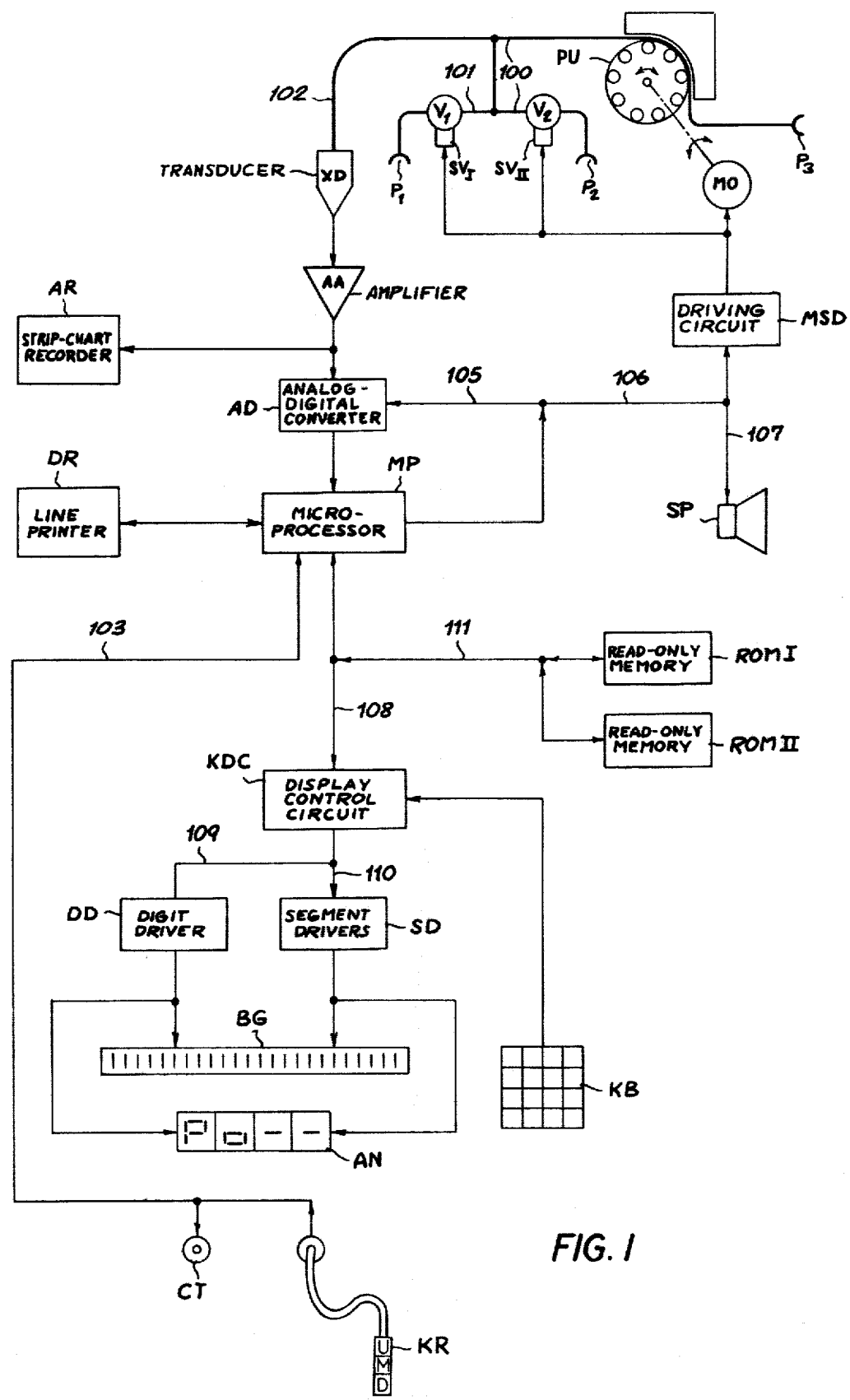
FIG. 1 is a block diagram of an ocular testing device according to my present invention.
Figure 2:
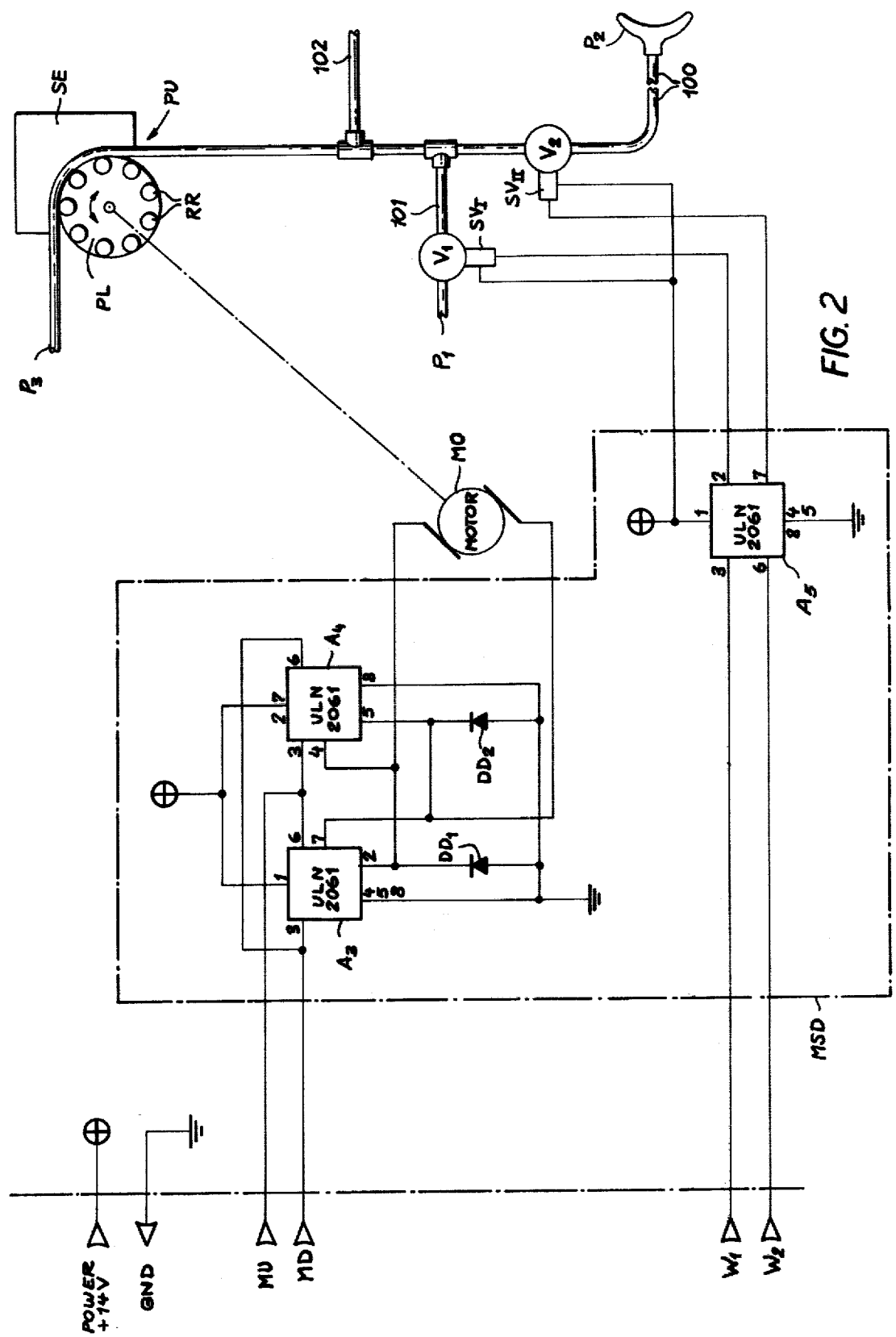
FIG. 2 is a partial circuit diagram showing details of a motor and valve driving circuit illustrated in FIG. 1.

As illustrated schematically in FIG. 1 and in detail in FIG. 2, a device according to my present invention for testing a patient for carotid occlusive disease comprises an eye cup $P_2$ (see U.S. Pat. No. 3,308,810 issued Mar. 14, 1967) engageable with an external surface of a person's eye and connected to a flexible duct or tube 100. At another end $P_3$ of tube 100 is disposed a peristaltic pump PU for generating a vacuum in tube 100 upon the engagement of cup $P_2$ with an eye surface. Pump PU includes a multiplicity of rollers RR rotatably attached to a periphery of a circular plate PL for squeezing or collapsing portions of tube 100 against a shoe SE, whereby incremental volumes of air may be successively withdrawn from tube 100. Plate PL is turned by a motor MO under the control of a driving circuit MSD described in detail hereinafter.

Tube 100 is connected via a duct branch 101 to a first valve $V_1$ operated by a solenoid $SV_1$ for normalizing the pressure level in the tube, i.e. for restoring the tube to the ambient atmospheric pressure. A second valve $V_2$ operated by a solenoid $SV_2$ closes an end of tube 100 proximate to eye cup $P_2$ during calibration of the device according to my invention. As shown in FIG. 1, tube 100 is connected through a duct branch 102 to a transducer XD which feeds analog signals to an amplifier circuit AA. Amplifier AA works into a strip chart recorder AR for continuously recording pressure levels monitored by transducer XD and into an analog-digital converter AD tied at an output to a microprocessor MP. Microprocessor MP receives further inputs from a keyboard KB via a display and keyboard control circuit KDC and from a remote pushbutton unit KR via a bidirectional multiple 103 also extending to a camera trip CT. Output multiples 105 and 106 extend from microprocessor MP to analog-digital converter AD and to driving circuit MSD, respectively, multiple 106 having a lead 107 working into a speaker SP. Keyboard and display control circuit KDC communicates with the microprocessor via a bidirectional multiple 108 and with digit and segment driving circuits DD and SD via multiples 109, 110. Digit drivers DD and segment drivers SD are each connected to a bar graph BG and to an alpha-numeric display AN for showing pressures sensed by transducer XD and the results of computations performed by microprocessor MP. The microprocesor MP feeds a line printer DR and exchanges data with a pair of read-only memories $ROM_1$, $ROM_2$ via a bidirectional multiple 111.

Figure 3:
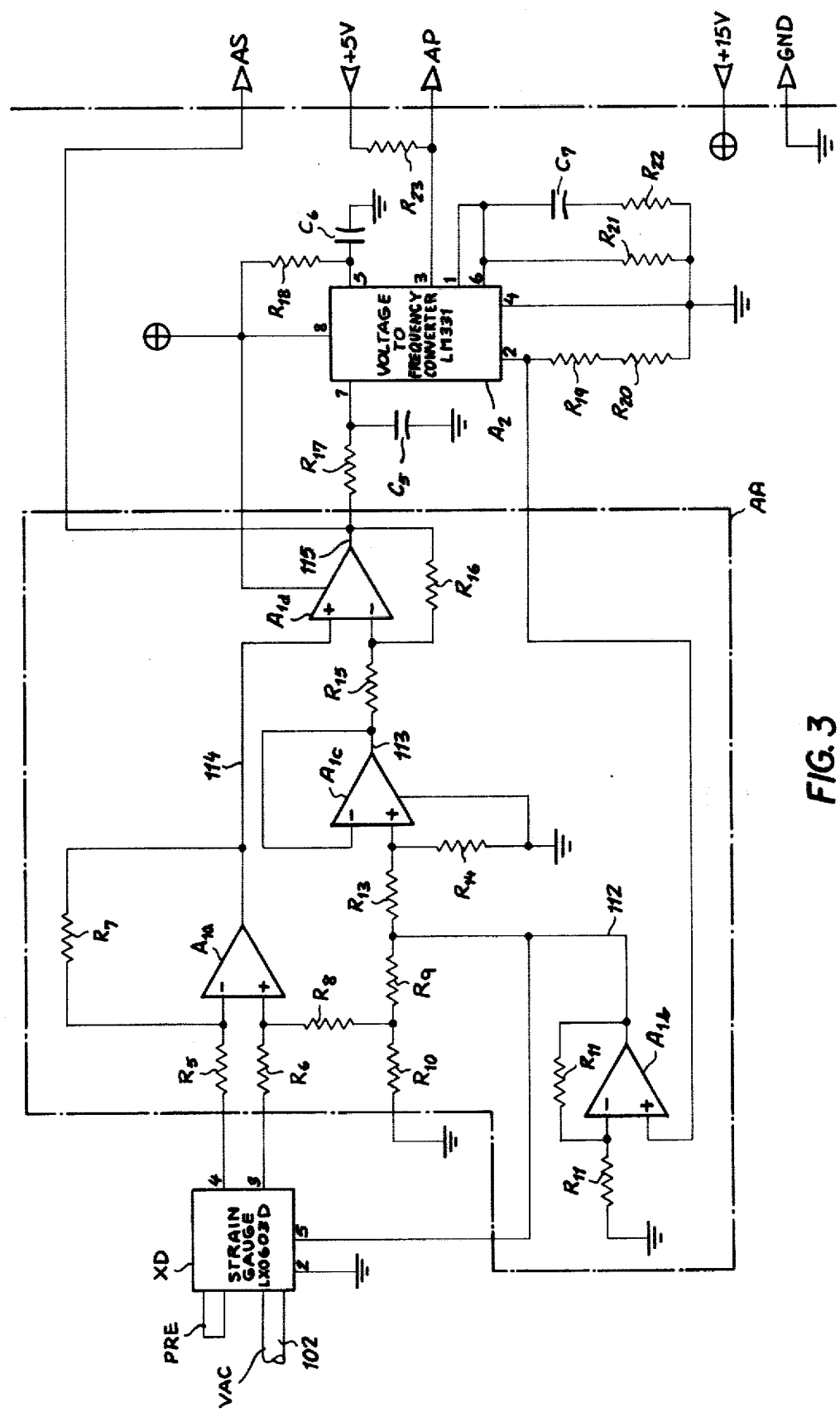
FIG. 3 is a circuit diagram of an amplifier shown in FIG. 1.

As illustrated in FIG. 3, amplifier circuit AA includes a summing and differencing amplifier $A_{1a}$ connected at an inverting input via a resistor $R_5$ to pin No. 4 of a bridge strain gauge, National Semiconductor model No. LX0603D, serving as transducer XD. Amplifier $A_{1a}$ is connected at a non-inverting input to pin No. 3 of strain gauge LX0603D via a resistor $R_6$ and to ground over two resistors $R_8$ and $R_{10}$. Pin No. 2 of the strain gauge is grounded, while pin No. 5 is tied to an output lead 112 of a scaling-up amplifier $A_{1b}$ for energizing strain gauge LX0603D with a 7.5-volt supply. Lead 112 providing a fixed reference voltage of 7.5 volts also works into the non-inverting input of amplifier $A_{1a}$ over resistor $R_8$ and a resistor $R_9$ and into a non-inverting input of a third amplifier $A_{1c}$ via a resistor $R_{13}$, this input being shunted to ground over a resistor $R_{14}$. Amplifier $A_{1c}$ has an output lead 113 providing feedback to an inverting input of another amplifier $A_{1d}$ over a resistor $R_{15}$, amplifier $A_{1d}$ having a non-inverting input linked to an output lead 114 of amplifier $A_{1a}$. Lead 114 is tied to the inverting input of amplifier $A_{1a}$ via a resistor $R_7$.

Amplifier $A_{1d}$ has an output lead 115 carrying an analog signal AS fed to a remote analog output unit formed as the strip chart recorder AR, fed back to the inverting input of amplifier $A_{1d}$ over a resistor $R_{16}$ and transmitted to an input of voltage-to-frequency converter $A_2$ over a resistor $R_{17}$. In particular, lead 115 may be connected to pin No. 7 of a National Semiconductor converter model No. LM331, this pin being grounded through a capacitor $C_5$ serving as a high-frequency filter. Pins Nos. 1,2,4,6 of the voltage-to-frequency converter LM331 are connected to a normalization circuit including resistors $R_{19}$, $R_{20}$, $R_{21}$, $R_{22}$ and capacitor $C_7$, while pin No. 5 is tied to a supply of 15 volts via a resistor $R_{18}$ and to ground via a capacitor $C_6$. Pin No. 2 is connected to a noninverting input of amplifier $A_{1b}$ for supplying same with a 1.9-volt reference potential, this amplifier having an inverting input which is grounded via a resistor $R_{12}$ and which is linked to output lead 112 via a resistor $R_{11}$. Converter LM331 generates on pin No. 3 a rectangular output wave AP having a constant pulse width of 20 msec and a frequency varying from 5 KHz to 45 KHz. Pin No. 3 is connected to a 5-volt source via a resistor $R_{23}$; pin No. 8 is tied to the 15-volt supply.

Figure 4:
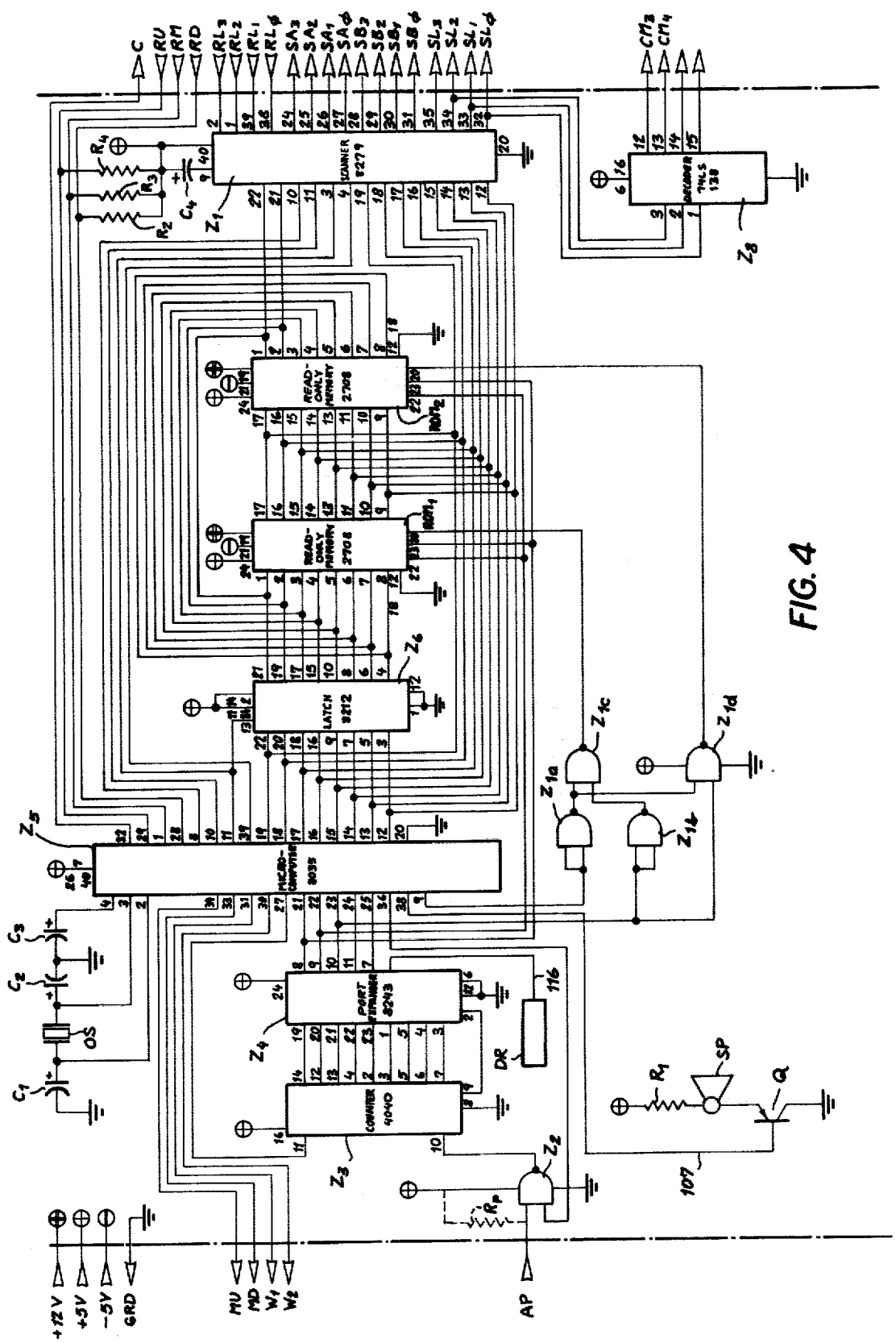
FIG. 4 is a circuit diagram in part illustrating connections between a microprocessor and read-only memories shown in FIG. 1.

In FIG. 4 I have shown in detail the connections of read-only memories $ROM_1$ and $ROM_2$ to a microcomputer $Z_5$ essentially comprising microprocessor MP. Read-only memories $ROM_1$ and $ROM_2$ are advantageously formed as erasable programmable read-only memories, National Semiconductor model No. 2708, tied directly to 8 terminals or pins of an Intel IC chip 8035 forming microcomputer $Z_5$ and indirectly to these same terminals over an address latch $Z_6$ advantageously constituted by an Intel chip No. 8212. Microcomputer chip 8035 is linked to a counter $Z_3$ by means of a port expander $Z_4$, which also energizes line printer DR via a multiple 116, and by means of a NAND gate $Z_2$ which receives rectangular wave AP from converter $A_2$ (FIG. 3); pin No. 36 of microcomputer chip 8035 is connected to an input of NAND gate $Z_2$ for enabling the same to energize its output in response to rectangular wave AP, gate $Z_2$ emitting a clock signal for stepping counter $Z_3$. This counter may be a National Semiconductor chip No. 4040 whose pin No. 11 is linked to pin No. 27 of microcomputer chip 8035 for receiving a clearing or resetting signal therefrom.

As illustrated in FIG. 4, lead 107 (FIG. 1) extends from microcomputer chip 8035 to a transistor $Q_1$ for driving speaker SP, a driving coil (not shown) in the speaker being operationally connected at one end to ground over transistor $Q_1$ and at an opposite end to a 5-volt source over a 50-ohm resistor $R_1$. Microcomputer terminals or pins Nos. 9 and 23 are tied to pins No. 20 of read-only-memory chips 2708 via enabling circuitry comprising four cascaded NAND gates $Z_{1a}$, $Z_{1b}$, $Z_{1c}$, $Z_{1d}$, while pins Nos. 2,3,4 work into an oscillator circuit including a pair of 20 pF mica capacitors $C_1$ and $C_2$, a 1 mF capacitor and a 6 MHz oscillator OS. The microcomputer chip 8035 supplies to the driving circuit MSD (FIGS. 1 and 2) signals MU and MD for rotating motor MO in a forward or a reverse direction, thereby either decreasing or increasing the pressure in tube 100, and signals $W_1$ and $W_2$ for opening solenoid valves $SV_1$ and $SV_2$, respectively, thereby either restoring tube 100 to atmospheric pressure or depressurizing cup $P_2$ upon engagement thereof with a patient's eye.

Microcomputer chip 8035 and read-only-memory chips 2708 are connected to a scanning and buffer-register circuit $Z_7$ which includes a counter emitting strobe signals $SL_0$–$SL_3$ directly and strobe signals $CM_0$–$CM_3$ indirectly over a decoder $Z_8$. In response to commands from the microcomputer $Z_5$, IC No. 8035, scanner $Z_7$ generates signals $SA_0$–$SA_3$ and $SB_0$–$SB_3$ for energizing LED segments in bar graph BG and alpha-numeric display AN (see FIGS. 1 and 5). The scanner $Z_7$ receives signals $RL_0$ and $RL_3$ from keyboard KB (see FIG. 5) upon the depression of pushbuttons thereof and upon the enabling of respective key groups by strobe signals $CM_0$–$CM_3$, keyboard KB including buttons for the selection of digits and further buttons $F_1,F_2$ EOT, REV, %, CLR for the selection of operating modes or of particular functions such as clearing memory circuits. Scanner $Z_7$ and decoder $Z_8$ may be constituted by IC chips Intel model No. 8279 and National Semiconductor model No. 74LS138.

As shown in FIGS. 4 and 5, remote control KR emits to microcomputer chip terminals Nos. 29, 1, 28 signals RU, RM, RD for decreasing the pressure in tube 100 (FIGS. 1 and 2), for storing pressure values in microcomputer memory stores and for increasing the pressure in tube 100, respectively. Leads carrying signals RD, RM and RU are tied to a 5-volt source via resistors $R_2$, $R_3$, $R_4$, thereby generally energizing microcomputer pins Nos. 28, 1, 29; thus, actuation of respective pushbuttons on remote control unit KR induces a voltage drop which comprises signals RU, RM, RD. FIG. 4 also shows a 5-volt source connected indirectly to pin No. 9 of scanner chip 8279 and directly to terminal No. 40 thereof for resetting or clearing stack registers in this chip and for initializing counter operations.

As illustrated in FIG. 5, signals $SL_0$–$SL_3$ are fed to a decoder $Z_9$ which emits signals to a pair of inverter/-buffer registers $Z_{10}$, $Z_{11}$ in turn working into respective digit drivers $Z_{12}$, $Z_{13}$. Digit drivers $Z_{12}$, $Z_{13}$ transmit enabling signals $D_1$–$D_{12}$ to alpha-numeric display AN and to bar graph BG, energization of individual LED segments in the two displays being determined by signals $SA_0$–$SA_3$ and $SB_0$–$SB_3$ received from scanner circuit $Z_7$ (IC No. 8279, FIG. 4) via segment drivers $Z_{14}$ and a current-limiting resistor array RA. Bar graph BG may include 8 groups of 8 parallel LED segments a'–h' shown in detail in FIG. 6; alpha-numeric display AN advantageously comprises 4 groups of 7 LED segments a"–g" disposed in a figure-8 arrangement shown in detail in FIG. 7. Segments a"–g" are connected to respective outputs a–g of resistor array RA, all the segments of any group of display AN being connected to one terminal of digit-driving circuit $Z_{13}$. Thus, 4 terminals of digit driver $Z_{13}$ are tied to respective segment groups of display AN for enabling via signals $D_1$–$D_4$ the energization of segments a"–g" according to signals a–g.

The functions of decoder $Z_9$, inverter/buffers $Z_{10}$ and $Z_{11}$, digit drivers $Z_{12}$ and $Z_{13}$ and segment driver $Z_{14}$ are expediently performed by IC chips National Semiconductor model Nos. 74LS154, 74LS04, 75492 and Sprague model No. UDN2981, resistor array RA advantageously consisting of a Fairchild model No. RA08. As shown in FIGS. 4 and 5, microcomputer $Z_5$ (chip 8035) generates a signal CC for actuating camera trip CT which operates a camera shutter (not shown) through a camera interface CI.

In FIG. 2 I have shown three Darlington drivers $A_3$, $A_4$, $A_5$ (Sprague model No. ULN2061), driver $A_5$ being connected to microcomputer $Z_5$ (FIG. 4) and to solenoid valves $SV_1$, $SV_2$ for actuating the same in response to signals $W_1$ and $W_2$ and drivers $A_3$, $A_4$ being tied to microcomputer $Z_5$ and to motor MO for reversibly energizing the same under the control of signals MU and MD. The motor control circuit includes a pair of diodes $DD_1$ and $DD_2$ for the dynamic braking of motor MO.

It is to be noted that in designing a device according to my present invention, resistors $R_9$, $R_{15}$ and $R_{20}$ shown in FIG. 3 are selected for adjusting a zero-offset, for adjusting gain, and for setting the frequency and pulse-width output of converter $A_2$. Thus, resistor $R_9$ has a magnitude selected to reduce to zero the voltage difference between output lead 113 and 114 of amplifiers $A_{1c}$ and $A_{1a}$ upon the equalization of pressure levels at a positive-pressure or atmospheric input PRE of strain gauge LX0603D and a negative-pressure or vacuum-sensing input VAC, this input being connected to duct branch 102 of tube 100 (FIGS. 1 and 2). Upon the application to input VAC of a negative pressure of a predetermined maximum magnitude, the size of resistor $R_{15}$ is chosen so that signal AS has a maximum amplitude, thereby optimizing the gain of amplifier circuit AA. Voltage-to-frequency converter $A_2$ has an output signal AP of 5 KHz (pulses of 20 μsec duration separated by 200 μsec) at zero input voltage, i.e. when signal AS is zero, and resistor $R_{20}$ is selected for giving signal AP a frequency of 45 KHz at the maximum amplitude of signal AS.

Upon turning on a device according to my present invention, data stores and stack registers in microcomputer $Z_5$ (chip 8035, FIG. 4) and scanner $Z_7$ (chip 8279) are cleared and a message appears on alpha-numeric display AN indicating that a calibration procedure hereinafter described is to follow.

Initially valves $SV_1$ and $SV_2$ are closed. Microcomputer $Z_5$ emits signals MU, MD to motor-control circuit MSD for inducing the motor MO to rotate roller plate PL in a counterclockwise direction, thereby drawing air from tube 100. After one minute of motor operation, the negative pressure in tube 100 has reached a maximum calibration level whose magnitude varies as a function of temperature and of other operating conditions. An expected value for this maximum negative pressure is 740 mm Hg. After this one minute of motor operation vacuating tube 100, microcomputer $Z_5$ stops the motor and emits a pulse of 20 msec duration to NAND gate $Z_2$, enabling the transmission to counter $Z_3$ of stepping signal AP. Computer $Z_5$ stores the number of counts made by unit $Z_3$ (FIG. 4) during the 20 msec interval, this number being proportional to the vacuum pressure magnitude in tube 100 (the number may be as high as 1000 counts for a negative pressure of 740 mm Hg). One or both valves $SV_1$, $SV_2$ are then opened in response to signals $W_1$, $W_2$ and within several seconds the tube is restored to the ambient atmospheric pressure. Microcomputer $Z_5$ again enables NAND gate $Z_2$ and stores the number of counts made by unit $Z_3$ during a 20 msec interval at atmospheric pressure. This number will be approximately 100. Logic circuitry in the microcomputer $Z_5$ then makes a scale adjustment including a calculation of the slope between the minimum and maximum pressure levels. Any drifting due to temperature variations or any other changed conditions is automatically compensated for.

After a calibration interval lasting approximately 1 minute and 5 seconds, the word "test" appears on alpha-numeric display AN, indicating that an operator is to push a button of keyboard KB selecting a mode of operation, i.e. a test to be performed. Let us assume that one or more keys are actuated for initiating an ophthalmodynamometric test for diagnosing carotid occlusive disease. Let us also assume that the operator chooses direct display of negative pressures applied to a patient's eye. A key may also be actuated for indicating whether the test is going to be applied first to the right eye or to the left eye. Let us assume the right eye is first.

During the operation of the device according to my present invention, keyboard (see FIG. 5) is continuously scanned by signals $CM_0$-$CM_3$. Thus, if a key $F_2$ is pushed for selecting initial testing of the right eye, signal $RL_1$ (FIGS. 4,5) will be energized upon the appearance of strobe signal $CM_3$.

Upon the treatment of the patient's eyes with an anesthetic and a pupil dilator, a physician directs the patient to look toward his own left. Eye cup $P_2$ (FIGS. 1 and 2) is then placed on the sclera of the patient's right eye and a pushbutton U of remote control KR (see FIG. 1) is actuated for decreasing the pressure in tube 100. The physician observes the main artery of the retinal surface of the patient's eye and, upon noting a pulsation of the retinal artery, releases button U and actuates a memory button M on remote control KR, thereby storing in microcomputer $Z_5$ the magnitude of the negative pressure being applied to the eye. Thhe above-described procedure may be repeated to verify the pressure level at which the retinal artery first begins to pulsate, the physician depressing a remote-control key D which transmits signal RD to microcomputer $Z_5$ for causing the same to reverse the direction of rotation of motor MO and thereby decrease the vacuum in tube 100. The negative pressure being applied to the eye upon pulsation of the retinal artery corresponds to the diastolic pressure in the right internal carotid artery. Upon the reactuation of remote memory button M, any value previously stored in the microcomputer and assigned to the diastolic pressure of the patient's right internal carotid system is erased and the presently measured negative pressure level is stored. Of course, it is also possible for a plurality of negative pressure magnitudes to be stored, microcomputer $Z_5$ subsequently performing arithmetic operations for determining an average diastolic negative-pressure value. It is to be noted that micro-computer $Z_5$ makes the pressure measurements by means of counter $Z_3$.

Upon the taking of the diastolic measurements for the right eye, the physician actuates a button on keyboard KB signaling the microcomputer that this portion of the test is over and that the recorded negative-pressure magnitude is to be stored in a memory location unaffected by future depressions of remote-control key M. Let us call this button the end-of-test button (EOT). The physician then pushes remote-control key U, thereby further decreasing the negative pressure in tube 100 and in the eye cup $P_2$. Upon observing (with an ophthalmoscope, preferably) the collapse of the retinal artery, the physician releases the vacuum-increasing key U and pushes button M, storing a negative-pressure magnitude corresponding to the systolic pressure in the patient's right internal carotid artery system. As heretofore described, the procedure may be repeated for determining more precisely the pressure at which the retinal artery collapses. Upon the depression of keyboard key EOT, microcomputer $Z_5$ stores a pair of negative pressure values associated with diastolic and systolic pressures of the patient's right carotid artery system. The physician then actuates key D and releases cup $P_2$ from the patient's right eye. Alternatively, microcomputer $Z_5$ may be programed to automatically repressurize tube 100 by opening valve $V_1$ upon the second actuation of keyboard button EOT, i.e. upon the storing of the systolic negative-pressure magnitude.

During the testing of a patient's eye, the magnitude of the negative pressure being applied to the eye is displayed as a roving illuminated segment on bar graph BG and as an updated numeral on alpha-numeric display AN, this display also indicating by an "R" or an "L" whether the right eye or the left eye of the patient is being tested. Upon the actuation of remote-control button M, the magnitude of the vacuum in tube 100 is stored in microcomputer $Z_5$ and is displayed on bar graph BG as a fixed illuminated segment. The light-emitting LED segment continues to be energized by microcomputer $Z_5$ upon the actuation of keyboard button EOT transferring the pressure valve to another memory location. Thus, two LED segments of bar graph BG are energized at any time during the determination of the patient's systolic negative-pressure level: one segment is fixed by the previous depression of key EOT and corresponds to the patient's diastolic pressure for the eye being tested and another segment depends to the negative pressure then being applied to the eye.

Upon a second actuation of key EOT, the values of the negative pressures corresponding to diastolic and systolic pressures are displayed on bar graph BG as a pair of fixed illuminated segments.

Keyboard KB includes review button REV for inducing alpha-numeric unit AN to display pressure values stored in the microcomputer's memory. An initial actuation of this button will cause a first recorded pressure magnitude to be displayed together with an "R" or an "L" indicating which eye the measurement was taken for, a subsequent actuation of key REV causing a second recorded pressure to be displayed.

Upon the release of cup $P_2$ from the patient's right eye, and upon possible review of the recorded diastolic and systolic negative-pressure magnitudes by the depression of button REV, a third actuation of key EOT will reinstate an input mode in the device according to my present invention. Microcomputer $Z_5$ is now informed via keyboard KB that the left eye of the patient is to be tested. The above described procedure is then repeated for the left eye. At the end of the testing, i.e. upon the fifth actuation of end-of-test button EOT, four vacuum magnitudes are stored in the microcomputer and may be recalled to display AN with four consecutive actuations of key REV, in each case a respective eye being indicated. A first depression of a key labeled "%" will display the percentage difference, as calculated by microcomputer $Z_5$, between the systolic pressure magnitudes recorded for the left eye and the right eye; a second depression of this key will display the percentage difference between the two stored diastolic pressure levels. Actuation of yet another key CLR will clear memories in microcomputer $Z_5$ of all stored data and return the device to an input mode awaiting selection of a further test to be performed.

In order to test the patient for unilateral carotid occlusive disease, the physician compares the calculated percentage differences for diastolic and systolic pressure values with predetermined standards. An exceeding of these standards is diagnosed as an occlusion in the carotid artery system of the side having the greater pressure levels. Bilateral carotid occlusive disease may also be diagnosed through use of the device according to my present invention. Upon selection of the ophthalmodynamometric mode of operation, the age of the patient together with the axial lengths and initial intraocular pressures of the patient's eyes are entered into the microcomputer $Z_5$ via keyboard KB. The left and right brachial pressures of the patient are also fed to the computer. Testing then proceeds as heretofore described with respect to the determination of unilateral carotid occlusive disease. However, the data now stores in the microcomputer's memories and displayed by units BG and AN are approximate retinal-artery blood pressures calculated by microcomputer $Z_5$ according to a pre-established algorithm, this algorithm making corrections for the hardening of arteries with increasing age and for the different negative pressures needed to raise to the same level the internal pressures of eyes of different sizes. Upon completion of data acquisition, four consecutive depressions of a button APD on keyboard KB will cause the display on unit AN of the absolute diastolic and systolic pressure differences between the calculated retinal-artery pressures and the brachial pressures for the left and right upper vascular systems. Bilateral carotid occusive disease may be diagnosed if these pressure differences exceed pre-established standard reference values. Unilateral carotid occlusions may also be diagnosed, absolute diastolic and systolic pressure differences being calculated between the left and the right eye.

Another mode of operation of a device according to my present invention is a test for determining the rate of aqueous outflow, which is utilizable in the diagnosis of glaucoma. A pre-established negative pressure is applied to a patient's eye by microcomputer $Z_5$ via eye cup $P_2$. Using an applanation tonometer, a physician measures an initial intraocular pressure and thereupon actuates remote-control button M for initiating a counting procedure performed by microcomputer $Z_5$ for measuring out a time interval of a predetermined duration. Fifteen seconds before the end of this time interval, microcomputer energizes speaker SP (FIGS. 1 and 4) to emit a recurrent tone, thereby informing the examining physician that a final tonometric measurement is imminent. After the fifteen seconds, the tone becomes steady and the physician performs a second and final measurement. A depression of remote-control button D or of keyboard button EOT will terminate the emission of sound by the speaker and release the eye cup $P_2$ from the patient's eye. Upon the entering into the microcomputer of the initial and final intraocular pressures and of the axial length of the eye being tested, the device will display on unit AN a calculated aqueous outflow rate for that eye. Speaker SP may also be energized by microcomputer $Z_5$ upon the loading of pressure data into the computer's memory.

Another mode of operation relates to fluorescent retinography. A camera's trip cable is connected to camera-trip socket CT (FIGS. 1 and 5) and a number is fed to the microcomputer $Z_5$ for determining a recurrent pressure decrease. Upon the juxtaposition of a patient's eye to a slit lamp, cup $P_2$ is placed upon the eye's surface and the vacuum in the cup decreased until the collapse of the retinal artery (systolic pressure level). A dye is then injected into the patient's blood stream and, after a predetermined time interval, remote-control button M is actuated for initiating a procedure comprising the tripping of the camera's shutter and a subsequent decrease of the pressure in tube 100 and cup $P_2$ by an amount equal to the number previously entered into the microcomputer. Upon stabilization of the pressure system of the eye and artery and the resetting of the camera for another exposure, the procedure is repeated. The above-described sequence continues until a predetermined number of photographs have been taken, whereupon speaker SP emits a a tone and microcomputer $Z_5$ releases the cup from the patient's eye. Two depressions of button REV will display on unit AN the initial pressure (systole) and the pressure at which the final photograph was taken.

I claim:

1. A method of testing a patient for internal carotid occlusive disease, comprising the steps of:
    applying negative pressure with a continuously increasing magnitude to a surface of one eye of said patient to monotonically increase the pressure within said eye to the diastolic pressure level and to the systolic pressure level of the retinal artery of said eye;
    observing the retinal artery of said eye with an opthalmoscope;
    electronically storing, upon detecting pulsation of said artery, a first magnitude related to the negative pressure being applied to said eye upon the pulsation of said artery and, upon detecting a cessation of pulsation of said artery, a second magnetude related to the negative pressure being applied to said eye upon cessation of pulsation;

applying negative pressure with a continuously increasing magnitude to the other eye of said patient to monotonically increase the pressure within said other eye to the diastolic pressure level and to the systolic pressure level of the retinal artery of said other eye;

electronically storing, upon detecting a pulsation of the retinal artery of said other eye, a third magnitude related to the negative pressure being applied to said other eye upon pulsation of the retinal artery thereof and, upon detecting and cessation of pulsation of the retinal artery of said other eye, a fourth magnitude related to the negative pressure being applied to said other eye upon cessation of pulsation of the retinal artery of said other eye;

automatically calculating a percentage difference between said first magnitude and said third magnitude and another percentage difference between said second magnitude and said fourth magnitude; and comparing said percentage differences with pre-established limits, whereby an embolism of an internal carotid artery system may be diagnosed.

2. A method as defined in claim 1 wherein said first magnitude and said third magnitude are the magnitudes of negative pressures being applied to said one eye and to said other eye, respectively, upon attainment of the diastolic pressure of the retinal artery of the respective eye and said second magnitude and said fourth magnitude are the magnitudes of negative pressures being applied to said one eye and to said other eye, respectively, upon the attainment of the systolic pressure of the retinal artery of the respective eye.

3. A method as defined in claim 1 further comprising the steps of determining the age of said patient and the axial lengths and initial pressures of said one eye and of said other eye, wherein said magnitudes are approximate retinal-artery pressures automatically calculated according to an algorithm making corrections for the hardening of the arteries due to increasing age and for a negative-pressure differential due to variable eye size.

4. A method as defined in claim 3 further comprising the steps of measuring left and right brachial pressures, diastolic and systolic, and comparing said retinal-artery pressures to said brachial pressures, whereby bilateral internal carotid occlusive disease may be diagnosed.

5. A method as defined in claim 1, further comprising the step of automatically displaying said magnitudes.

6. A device for testing a patient for internal carotid occlusive disease, comprising:

a cup engageable with the sclera of a person's eye;

vacuum-generating means including a peristaltic pump and a flexible tube connected to said cup for applying negative pressure with a substantially continuously increasing magnitude to an external eye surface, thereby monotonically raising the intraocular pressure of the respective eye to the diastolic pressure level and to the systolic pressure level of the retinal artery of such respective eye;

a transducer connected to said vacuum-generating means for producing electronic signals in response to negative pressures applied to an eye;

a microprocessor connected to said transducer for directly storing magnitudes at least partially determined by the diastolic and systolic pressures of the retinal arteries of a patient's left eye and right eye and for automatically calculating a percentage difference between magnitudes related to said diastolic pressures and another percentage difference between magnitudes related to said systolic pressures, said vacuum-generating means further including solenoid valves connected to said tube and operated under the control of said microprocessor;

display means connected to said microprocessor for showing in response to signals therefrom pressure magnitudes and calculated percentage differences; and a keyboard operatively connected to said microprocessor for feeding same patient-age and eye-size data and for selecting between a plurality of computer operation modes.

7. A device as defined in claim 6 wherein said transducer produces analog signals, further comprising a strip chart recorder connected to said transducer for continuously recording pressure variations and an analog-digital converter connected to said transducer and to said microprocessor for feeding digital signals thereto in response to analog output signals received from said transducer.

8. A device as defined in claim 7 wherein said analog-digital converter includes a voltage-to-frequency converter feeding square-wave pulses to a counter under the control of said microprocessor.

* * * * *